United States Patent [19]

Mauck et al.

[11] Patent Number: 5,085,986

[45] Date of Patent: Feb. 4, 1992

[54] DIAGNOSTIC TEST KIT AND METHOD FOR DETERMINATION OF CHLAMYDIAL ANTIGEN USING A MEMBRANE HAVING SURFACE HYDROXY GROUPS

[75] Inventors: John C. Mauck; Bradley P. Boyer, both of Rochester, N.Y.

[73] Assignee: Eastman Kodak Company, Rochester, N.Y.

[21] Appl. No.: 366,100

[22] Filed: Jun. 14, 1989

[51] Int. Cl.$^5$ ............................... G01N 33/571
[52] U.S. Cl. ........................... 435/7.36; 435/7.2
[58] Field of Search ............................ 435/7.36

[56] References Cited

U.S. PATENT DOCUMENTS

| 3,951,748 | 4/1976 | Devlin | 435/7.36 |
| 4,497,899 | 2/1985 | Armstrong et al. | 436/510 |
| 4,497,900 | 2/1985 | Abram et al. | 436/511 |
| 4,632,901 | 12/1986 | Valkirs et al. | 435/7.94 |

FOREIGN PATENT DOCUMENTS 173500  3/1986  European Pat. Off. .

OTHER PUBLICATIONS

U.S. Ser. No. 181,465 filed 4/15/88 by Shih, Warren III and Smith-Lewis.
U.S. Ser. No. 206,236 filed 6/13/88 by Snyder, Grogan and Sutton.
U.S. Ser. No. 255,920 filed 10/7/88 by Mauck.
U.S. Ser. No. 255,924 filed 10/7/88 by Pronovost and Gilbert.

*Primary Examiner*—Sam Rosen
*Attorney, Agent, or Firm*—J. Lanny Tucker

[57] ABSTRACT

Antigens from chlamydial organisms in specimens can be rapidly and sensitively determined using a polyamide microporous membrane which has surface hydroxy groups. This determination is accomplished by contacting extracted antigen with the polyamide microporous membrane for a sufficient time for the antigen to bind to the membrane. Antigen bound to the membrane is contacted with chlamydial antibody so as to form an immunological complex on the membrane. The presence of the complex on the membrane in then determined as a measure of the amount of chlamydial antigen present in the specimen. The use of this particular membrane improves reagent keeping and reduces background in the assay.

20 Claims, 4 Drawing Sheets

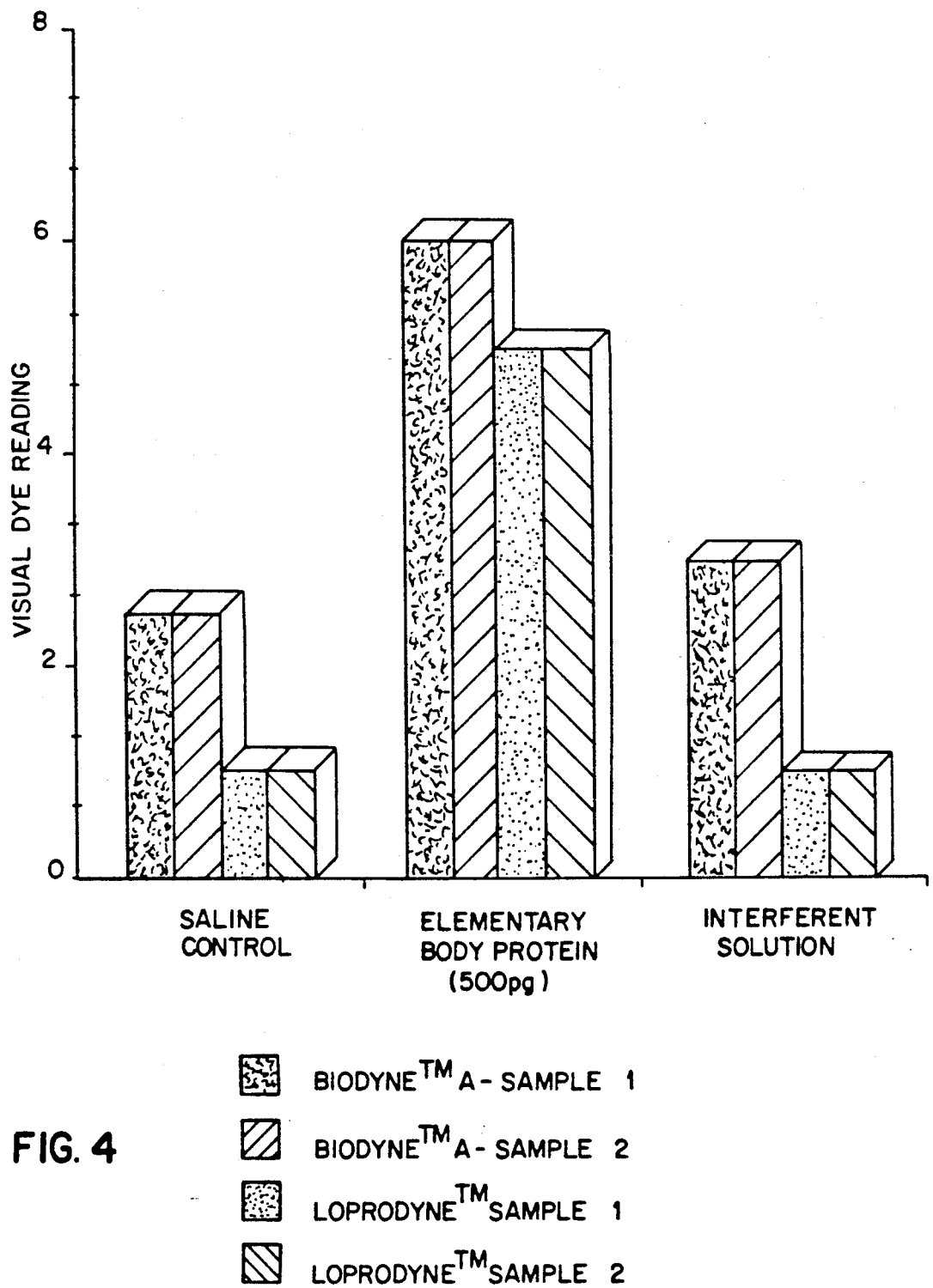

DIAGNOSTIC TEST KIT AND METHOD FOR DETERMINATION OF CHLAMYDIAL ANTIGEN USING A MEMBRANE HAVING SURFACE HYDROXY GROUPS

FIELD OF THE INVENTION

The present invention relates to a diagnostic test kit and method for the determination of chlamydial organisms. More particularly, it relates to a kit and method utilizing a polyamide microporous membrane having surface hydroxy groups.

BACKGROUND OF THE INVENTION

Immunoassays have been used in recent years to detect the presence of infectious diseases. In order for the assay to be useful, it must detect a particular organism with a high degree of reliability. In most cases, this requires the isolation and reaction of antigens peculiar to the organism with corresponding antibodies. For the test to be commercially successful, it also needs to be relatively inexpensive, long-keeping, simple to use and rapid.

One such organism which can be detected by immunoassay is *Chlamydia trachomatis* (herein *C. trachomatis*) which is one of two microbial species of the genus Chlamydiaceae, order Chlamydiales. There are 15 or more serotypes of this species which are the causes of a number of human ocular and genital diseases including trachoma, inclusion conjunctivitis, lymphogranuloma venereum, nongonococcal urethritis and proctitis. Infection from *C. trachomatis* is pervasive in the general population so that it is believed that there are millions of cases each year of nongonococcal urethritis alone.

Because of the widespread nature of these diseases, there is considerable interest in having a rapid, simple and reliable test for detection of chlamydial organisms. Assays for *C. trachomatis* carried out using a solid support are described in U.S. Pat. Nos. 4,497,899 (issued Feb. 5, 1985 to Armstrong et al). The described assays are performed by extracting antigen from the organism and coating it on a bare solid support. The coated antigen is then detected with either one or two antibodies, one of which is suitably labeled. The critical feature of the assays appears to be the use of a solid support for attachment which is untreated or uncoated with any material. Attachment of antigen is apparently achieved by incubating the coated support for an extended time sufficient to cause adsorption of antigen thereon. The entire assay described in U.S. Pat. No. 4,497,899 takes at least 3 hours to perform.

A much more rapid test for chlamydial organisms which has high reliability and can be performed at room temperature is described and claimed in U.S. Ser. No. 255,923 (filed on Oct. 7, 1988 by Pronovost). Our colleague found that ionically charged (specifically cationic) supports attract chlamydial antigen and enable one to quickly and sensitively detect the antigen.

A further improvement is described in U.S. Ser. No. 255,920 (filed Oct. 7, 1988 by Mauck) which describes the use of a surfactant-coated uncharged membrane in chlamydial assays. That invention enables one to rapidly and sensitively detect the antigen in biological specimens that contain copious amounts of whole blood, mucus or components thereof.

A large portion of the market for chlamydial assays is intended for doctors' offices where there is limited capacity for refrigeration of test kits. Thus, while the inventions described above provide important advances in the art, there is a further need to have reagents and test kits which can be stored for long periods of time without refrigeration before use while maintaining sensitivity and low background in the assay.

The current product marketed by Kodak as the Surecell ™ Chlamydia Test Kit has been received by the marketplace quite positively. It utilizes a disposable test device containing a surfactant-coated Biodyne ™ polyamide membrane like that described in the Mauck application noted above. It is highly desirable to increase the storage keeping of the reagents in that kit, and to keep the background in the assay low. This needs to be accomplished without the need for extensive refrigeration.

SUMMARY OF THE INVENTION

The needed improvements noted above are provided with a method for the determination of a chlamydial antigen comprising:

A. contacting chlamydial antigen extracted from a specimen suspected of containing chlamydial organisms with a polyamide microporous filtration membrane having a plurality of hydroxy groups on the surface thereof, and which has an average pore size of from about 1 to about 10 μmeter, for a sufficient time to bind the extracted antigen to the membrane, B. contacting chlamydial antigen bound to the membrane with chlamydial antibody, so as to form an immunological complex on the membrane, and C. determining the presence of the complex on the membrane as a measure of the presence of chlamydial organisms in the specimen.

This invention also provides a diagnostic test kit useful for the determination of a chlamydial antigen comprising:

a) a polyamide microporous filtration membrane having a plurality of hydroxy groups on the surface thereof, and which has an average pore size of from about 1 to about 10 μmeter, and b) antibodies to a chlamydial antigen.

The assay of this invention is rapid, reliable and simple to use. Generally, it can be carried out in less than 25 minutes at room temperature if desired. It is highly reliable for detecting extracted chlamydial antigen, and particularly the lipopolysaccharide antigen extracted from *Chlamydia trachomatis*. These advantages are also achieved with the invention described and claimed in U.S. Ser. No. 255,920 of Mauck (noted above).

However, the present invention achieves additional advantages because it provides a diagnostic test kit and assay which maintain high sensitivity and reduced background even after extended storage. Such advantages are achieved because the assay is carried out using a microporous polyamide membrane which has a plurality of surface hydroxy groups, as opposed to the surfactant-coated nonionic membrane of U.S. Ser. No. 255,920 (noted above).

BRIEF DESCRIPTION OF THE DRAWINGS

FIG. 4 is a bar graph illustrating the effect of high temperature keeping on reagents used in the assays of Example 5 below.

DETAILED DESCRIPTION OF THE INVENTION

Figure 1:
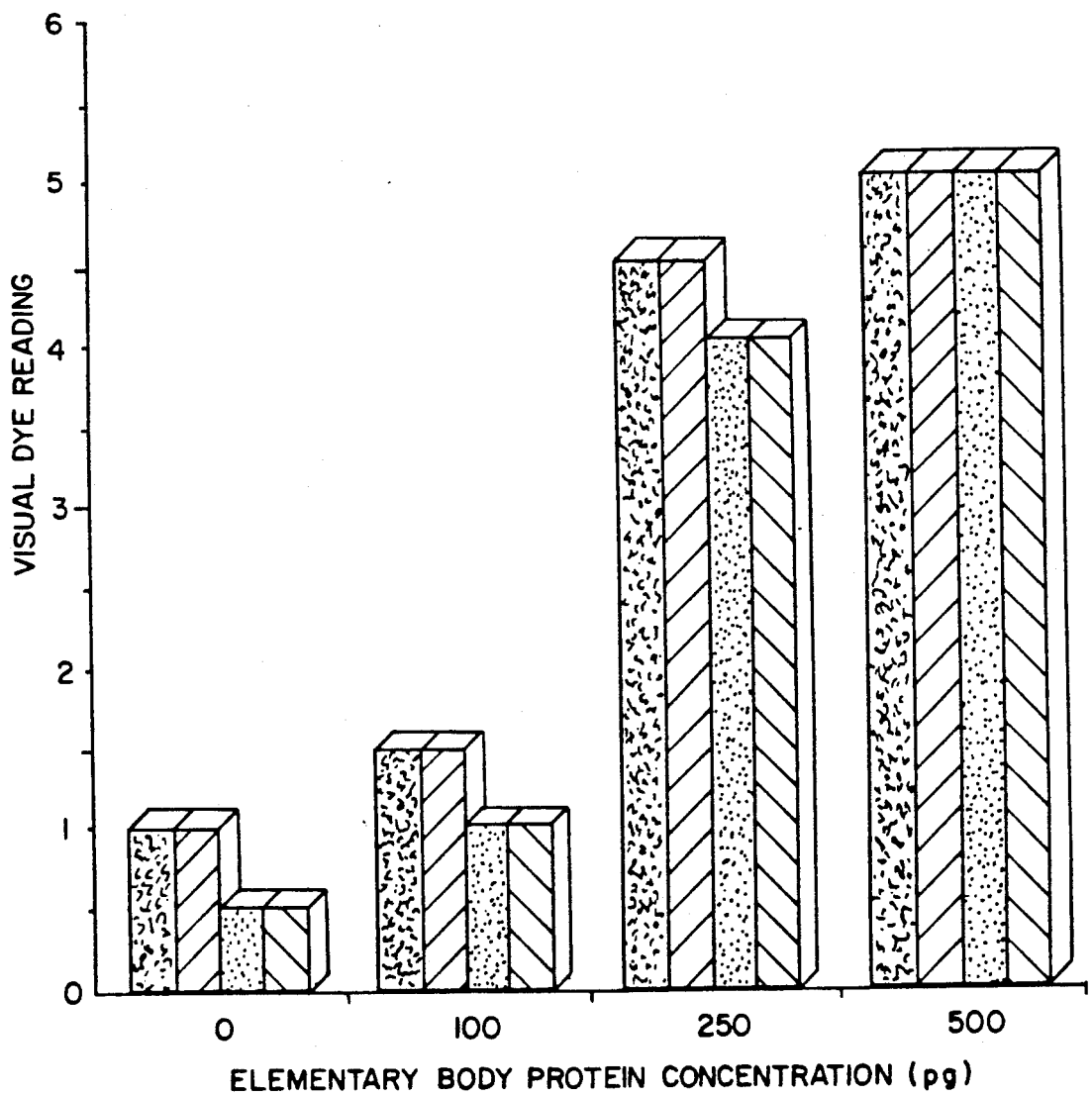
FIG. 1 is a bar graph showing the difference in sensitivity and background in an assay of the present invention as compared to assays using a surfactant-coated or plain unmodified nylon membrane. The illustrated data are discussed in more detail in Example 1 below.

The present invention comprises a method for determining the presence of *C. trachomatis* (or other chlamydial species) in a biological specimen which has been obtained from a patient using any suitable medical or diagnostic techniques. Such specimens include, for example, swab specimens obtained from the cervix, urethra, throat or anus of a patient, and body fluids such as synovial fluid or fluid from lesions. The biological specimens so obtained are suspected of containing bacterial organisms which comprise the chlamydial antigen (or mixture thereof) to be determined. The specimens are particularly likely to contain whole blood or mucus, and sometimes large amounts of both.

While the assay can be carried out to detect antigens from intact chlamydial organisms, it is usually desirable to extract the antigens from the organisms in order to increase assay sensitivity. Standard techniques can be used for lysing the organism to release antigen including, for example, solvent dilution or high pH lysing solutions, enzyme treatment and physical agitation such as sonication or centrifugation. Heating is described as a lysing technique in E.P. Publication 183,383 (published June 4, 1986). The use of anionic detergents or salts such as sodium dodecyl sulfate and deoxycholate is described in U.S. Pat. Nos. 4,497,899, 4,497,900 (both noted above) and 4,663,291 (issued May 5, 1987 to Rose).

In a preferred embodiment, the present invention can be used to detect the chlamydial lipopolysaccharide (glycolipid group) antigen (as described, for example, in E.P. Publication 193,431, published Sept. 3, 1986). Extraction procedures are also described therein. In another embodiment, the detected antigen can be the chlamydial major outer membrane protein of the organism which comprises about 60% of the total associated outer membrane protein. This antigen and methods of extraction are described in U.S. Pat. No. 4,427,782 (issued Jan. 24, 1984 to Caldwell et al). In some instances, a mixture of these chlamydial antigens will be detected using the present invention.

A preferred extraction composition is described in detail below in connection with the examples. The central feature of that composition is the presence of an alcoholamine or salt thereof and its high pH.

In addition, it may be desirable to use a protease in the extraction procedure to break down whole blood and mucus. A useful protease is described below in relation to the examples.

Once antigen is extracted from the organism, it is desirable, although not essential, that the specimen be prefiltered to remove cell debris, particulate matter and other unwanted materials prior to further handling. Prefiltering can be carried out in a suitable container having a filter of some type.

Extraction can be carried out in any suitable container, including devices specially designed for extraction of antigen. Useful devices are known in the art, including U.S. Pat. No. 4,746,614 (issued May 24, 1988 to Devaney, Jr. et al).

Extracted antigen is contacted with a polymeric microporous membrane having an average pore size of from about 1 to about 10 $\mu$meter, and preferably of about 5 $\mu$meter. The membrane is prepared from a polyamide, that is a long-chain synthetic polymer having recurring amide groups in the polymer backbone. They are generally copolymers of a diamine and a dicarboxylic acid, or homopolymers of a lactam of an amino acid. Representative materials include, but are not limited to, polyhexamethylene dodecanediamide (nylon 612), polyhexamethylene adipamide (nylon 66), poly-$\epsilon$-caprolactam (nylon 6), polyhexamethylene sebacamide (nylon 610) and poly-7-aminoheptanoamide (nylon 7), and mixtures thereof. Polyhexamethylene adipamide (nylon 66) is preferred.

The membrane material has been modified in some manner to provide a plurality of hydroxy groups on its surface. The number of such groups on the surface is not critical, however, sufficient number should be present to keep the background in the assay low, and to improve the reagent keeping in the test kit. It is uncertain as the reason for the improvement provided by hydroxy-group containing membranes as opposed to those where such groups are absent.

In one embodiment, the polymeric membrane is composed of a material which can be chemically modified before or after membrane formation to provide pendant hydroxy groups. Preferably, however, the polyamide is treated or modified with a second polymeric material which provides the hydroxy groups. This second polymeric material may be provided after the polyamide membrane has been formed, or simultaneously therewith. It can be covalently bonded to the polyamide, or attached in some other suitable manner. Generally, such second polymer is composed of polymerizable monomers, at least one of which provides the hydroxy groups. Many such monomers are known in the art, including for example, 2-hydroxyethyl methacrylate, 2-hydroxy acrylate, 1-hydroxy-2-(5-acryloxy-3-oxapentyl)naphthamide, 2-(1-hydroxy-2-naphthoylaminoethyl)acrylamide, 2-(2-hydroxy-4-m & p-vinylbenzyloxyphenyl)benzotriazole, N-hydroxymethyl diacetone acrylamide, m & p-hydroxymethylstyrene, N-(m-hydroxyphenyl)methacrylamide, N-(2-hydroxypropyl)methacrylamide, N-methylol acrylamide, N,N-dimethyl-N-(2-hydroxypropyl)amino methacrylamide, 1-glyceryl methacrylamide, 1,1-dihydroxymethyl-2-hydroxyethyl acrylamide and 2-(3,5-dihydroxybenzyloxyethyl)ethyl methacrylate.

The hydroxy-containing monomers can be polymerized to form homopolymers using standard technology, or they may be similarly copolymerized with one or more comonomers, such as styrene or a derivative thereof, acrylic and methacrylic acid esters, acrylamides, methacrylamides and any vinyl addition comonomers as long as the resulting copolymer does not have a deleterious effect on the hydroxy groups.

Examples of membranes having surface hydroxy groups and teaching of details about making them are provided in E.P. Publication 173,500 (published Mar. 5, 1986).

A particularly useful microporous membrane having the requisite porosity and surface hydroxy groups is commercially available from Pall Corp. as Loprodyne ™ microporous membranes.

The membrane is substantially free of particulate material, such as polymeric particles, which may be used for antigen capture, for example as described in E.P. Publication 264,036 (published Apr. 20, 1988).

In the practice of this invention, the membrane can be further treated by coating with a suitable nonionic surfactant, as described for example in U.S. Ser. No. 255,920 (noted above), but preferably such surfactant coating is not used.

The membrane described herein can be used in combination with other equipment (bottles, test tubes, swabs, beakers or cups) in order carry out the assay. Alternatively and preferably, it is fitted into a disposable test device in which the assay can be carried out and all fluids accommodated. Useful configurations of test devices are known in the art including U.S. Pat. Nos. 3,825,410 (issued July 23, 1974 to Bagshawe), 3,888,629 (issued June 10, 1975 to Bagshawe), 3,970,429 (issued July 20, 1976 to Updike) and 4,446,232 (issued May, 1984 to Liotta). Particularly useful devices are described and claimed in U.S. Pat. No. 4,833,087 (issued May 23, 1989 to Hinckley) and U.S. Ser. No. 240,179 (filed Sept. 6, 1988 by Hinckley et al).

The contact is carried out for a time sufficient for antigen to bind directly with the membrane. Generally, almost immediately upon contact of the antigen with the coated membrane, the antigen is bound thereto. The antigen is preferentially bound to the membrane as opposed to other proteins, cell components, whole blood or mucus or other debris which may be present in the test specimen or reagents used in the assay.

Generally within about 10 minutes, and preferably within 1 to 5 minutes, of the contact, the bound antigen is contacted with a reactive composition comprising a chlamydial antibody so as to form an immunological complex bound to the support. Fluid and unbound materials may be removed quickly at the same time. If the assay is carried out using a disposable test device, fluid and unbound materials (such as whole blood and mucus components) in the specimen are allowed to flow through the membrane and collected in a suitable compartment during the time the antigen is bound to the membrane.

The antibody used in this assay is specifically immunoreactive with one or more chlamydial serotypes (depending upon what organism is of interest). It can be polyclonal or monoclonal. If polyclonal, it is commercially available or prepared in various animals using known techniques employing an antigen common to the strain of organism to be detected. A single antibody or mixture thereof can be used. For example, antibody to either the chlamydial lipopolysaccharide or major outer membrane protein antigen, or antibodies to both antigens can be used in the assay. Preferably, the antibodies are monoclonal which are either commercially available or prepared using standard hybridoma technology. Useful procedures for preparing antibodies are described, for example, in E.P. Publication 193,431 and U.S. Pat. No. 4,427,782 (noted above).

In one embodiment, the antibody to the antigen is labeled for detection. Useful labels are known in the art and include chemical or biological compounds which are directly detectable using suitable procedures and equipment, as well as compounds which can be detected through further chemical or specific binding reactions to provide a detectable species. Examples of useful labels include radioisotopes, enzymes, fluorescent moieties, chemiluminescent moieties, phosphorescent moieties, biotin or its derivatives, avidin or its derivatives, ferritin, magnetizable particles, dyed particles, gold sols, dye sols, colored *Staphylococcus aureus* cells and others readily apparent to one skilled in the art. Radioisotopes or enzymes are preferred labels. The labels can be attached to antibodies using known techniques. Where the label is not directly detectable, further reagents or compounds are needed to render the reaction or specific binding product detectable. For example, if the label is biotin, it can be reacted with avidin which is conjugated with an enzyme to provide a detectable species. Where the label is an enzyme, such as glucose oxidase, urease, peroxidase, alkaline phosphatase and others, substrates in dye-providing compositions are also needed.

In a particularly preferred embodiment, the label is peroxidase, and at some point in the assay, hydrogen peroxide and a suitable dye-providing composition is added to provide a detectable dye. For example, useful dye-providing reagents include leuco dyes, such as triarylimidazole leuco dyes (as described in U.S. Pat. No. 4,089,747, issued May 16, 1978 to Bruschi), or other compounds which react to provide a dye in the presence of peroxidase and hydrogen peroxide (that is, compounds which react to provide a dye upon catalytic action of peroxidase).

In a preferred embodiment, the chlamydial antibody is not labeled, and detection of the antibody-antigen complex formed and bound to the membrane is accomplished using a second antibody (described below) which is specific to the unlabeled antibody and is appropriately labeled.

The chlamydial antibody can be provided in a reagent composition (also known as a blocking composition) further comprising one or more proteins which reduce nonspecific interactions on the support. Useful proteins are well known and include, for example, casein, α-casein, fetal bovine serum and porcine gamma globulin. A particularly useful reagent composition comprises a protein and an amphoteric surfactant, as described in relation to the examples below.

Once the bound antigen has been contacted with the chlamydial antibody, a bound immunological complex is formed on the membrane. To hasten the formation of this complex, the antibody and antigen are generally incubated at a temperature of from about 15° to about 30° C. for up to 10 minutes. Preferably, the incubation is carried out at from about 18° to about 25° C. (that is, room temperature) for from 1 to 5 minutes.

After the incubation and generally within about 10 minutes of the antibody-antigen contact, the bound complex is washed one or more times with a wash solution which generally has a pH of from about 7 to about 12. The solution preferably contains one or more surfactants to aid in separating unbound materials from the bound complex. Particularly useful surfactants are cationic surfactants, as described in relation to the examples below.

In the embodiment described above where the chlamydial antibody is labeled, the assay procedure after washing is to detect the label directly or indirectly after addition of the appropriate reagents. This is done relatively quickly after washing the bound complex, that is generally within about 10 minutes, and preferably within about 1 to about 5 minutes. If desired, label detection can be hastened with incubation if the reagents warrant it. The label is then detected using standard equipment and procedures.

In the preferred embodiment, the chlamydial antibody is unlabeled, and after washing the bound complex, it is contacted with an antibody directed to the unlabeled antibody. This second antibody (that is, an anti-antibody) is appropriately labeled with any of the labels described above. The antibody can be monoclonal or polyclonal and either purchased or prepared using known techniques. In a chlamydial assay, the anti-antibody is preferably a polyclonal antibody which is reactive with either of the lipopolysaccharide or major outer membrane protein antibodies.

After this contact, the resulting antigen-antibody-antibody complex which is bound to the coated membrane is incubated generally for up to about 10 minutes at a temperature of from about 15° to about 30° C., and preferably for about 1 to about 5 minutes at from 18° to 25° C.

Further washing is carried out to remove uncomplexed materials, and suitable enzyme substrates or other needed reagents are added to provide a detectable species. The bound antigen-antibody-labeled antibody complex is then detected on the membrane using standard radiometric, colorimetric, fluorescent or other detection techniques.

The diagnostic test kit of the present invention comprises the membrane described herein and one or more other component compositions, solutions or devices for carrying out the assay. For instance, it generally includes a reagent composition comprising an antibody (labeled or unlabeled) to a chlamydial antigen. Additional optional materials in the kit include wash solutions, dye-providing compositions, labeled anti-antibody compositions, extraction compositions, extraction devices, swabs or other specimen collecting means, disposable test devices and others known to one skilled in the art. Preferably, the kit includes the membrane provided as part of a disposable test device.

The following examples are provided to illustrate, but not limit the scope of, the present invention.

MATERIALS

Surecell TM test devices used in the assays contained 5 μmeter microporous filtration membranes available from Pall Corp. The devices used in the assays of the invention contained uncoated Loprodyne TM membranes, while the devices used in the Control assays contained Biodyne TM A membranes, some coated with Zonyl TM FSN nonionic surfactant, others used uncoated.

An interferent solution contained whole blood (25 μl), pig mucin (20 μl of 125 mg/ml in phosphate buffered saline solution, Sigma Chemical Co.), HL60 cells (5 μl, $5 \times 10^7$ cells/ml phosphate buffered saline solution, pH 7.2). The total volume was 50 μl.

The prefilter used was a 10 μmeter HDC filter available from Pall Corp.

An extraction device like that described in U.S. Pat. No. 4,746,614 (noted above) was used. It contained two separate dried coatings of: (1) tris(hydroxymethyl)aminomethane buffer (from 20 μl of a 1.65 molar solution, pH 11.1) with thimerosal preservative (0.01 weight %), and (2) a mixture of dithiothreitol (0.188 molar) from a solution (50 μl) of 2-(N-morpholino)ethanesulfonic acid buffer (10 mmolar, pH 6), sodium azide (1.54 mmolar), ethylenediamine tetraacetic acid (5.4 mmolar) dimedone (21.4 mmolar) and poly(acrylamide) (6.35 weight %).

The extraction composition comprised ethanolamine hydrochloride (0.47 molar), sodium chloride (0.27 molar), preservative (30 mmolar) disodium ethylenediaminetetraacetic acid (45 mmolar), Emcol TM CC-36 cationic surfactant (0.45 weight % from 10% solution in methanol, quaternary ammonium chlorides of polypropoxy-t-amine mixture from Witco Chemical), sodium azide (0.027 molar) and sodium hydroxide (0.66 molar, pH 13).

Antigen preparation: Serovar J antigen purified elementary bodies were obtained from Professor W. J. Newhall of Indiana University. Antigen solution (5 μl containing about 2900 ng antigen/μl) was diluted with bovine serum albumin in phosphate buffered saline solution (0.1 mg/ml, pH 7.2) to obtain a final concentration of about 500 pg, which was the amount usually added to each test well.

The mouse monoclonal antibody to the chlamydial lipopolysaccharide was prepared using standard hybridoma technology and a mouse cell line and stored in a solution of phosphate buffered saline solution (pH 7.2) containing sodium azide (0.01 weight %). An antibody reagent composition was prepared by adding a sample (19 μl) of the antibody solution to a phosphate buffered saline solution (diluting 1:800) containing casein (0.5 weight %) as a blocking protein and Lonzaine TM C amphoteric surfactant (0.01 weight %, available from Lonza Co.), then filtered through a 0.22 μmeter filter to obtain a working solution.

The labeled polyclonal antibody used was a goat anti-mouse IgG antibody conjugated to horseradish peroxidase (obtained from Bio-Rad). This conjugate was diluted to about 1:1000 in a phosphate buffered saline solution containing casein (0.5 weight %) and Lonzaine TM C amphoteric surfactant (0.01 weight %) then filtered through a 0.22 μmeter filter to obtain a working solution.

A protease solution contained Amideck TM protease (4 mg/ml, 170 units/mg, available from BioProducts Division, Eastman Kodak Co.) in 2-(N-morpholino)ethane sulfonic acid buffer (10 mmolar, pH 6), sodium chloride (50 mmolar), calcium chloride (5 mmolar), 1,2-propanediol (10% w/v) and preservative (0.01 weight %).

Another solution contained hydrogen peroxide (12 weight % in water), diethylenetriaminepentaacetic acid (10 μmolar) and preservative (0.01 weight %).

A wash solution comprised 3-cyclohexylamino-2-hydroxy-1-propanesulfonic acid buffer (0.05 molar, pH 10), Emcol TM CC-9 cationic surfactant (0.75 weight %) and preservative (0.01 weight %).

A control reagent solution was made up of creatine kinase-MB antibody (5 μg/ml), casein (0.5 weight %), Lonzaine TM C amphoteric surfactant (0.01 weight %) and preservative (0.01 weight %) in phosphate buffered saline solution (pH 7.2).

A dye-providing composition 2-(4-hydroxy-3-methoxyphenyl)-4,5-bis(4methoxyphenyl)imidazole leuco dye (0.008 weight %), poly(vinyl pyrrolidone) (1 weight %), sodium phosphate (10 mmolar, pH 6.8) diethylenetriaminepentaacetic acid (10 μmolar), 4'-hydroxyacetanilide (2 mmolar) and hydrogen peroxide (10 mmolar).

EXAMPLE 1

Assay for Chlamydial Lipopolysaccharide Antigen Using Various Membrane Materials This example compares the practice of the present invention with an assay for *C. trachomatis* using a disposable test device containing a membrane of the prior art. Two different samples of uncoated Biodyne ™ A membrane and two different samples of Loprodyne ™ were tested in the test devices.

The protease solution (about 280 μl) was added to several extraction devices, followed by samples (25 μl) of the solutions of various concentrations of elementary bodies, or a Control containing only phosphate buffered saline solution (25 μl). After mixing, the devices were held at room temperature for 3 minutes, and the extraction composition (280 μl) was added to each, followed by further incubation at room temperature for 3 minutes. The hydrogen peroxide solution (280 μl) was then added, and incubation continued for another 3 minutes.

The resulting mixtures (160 μl per well) were removed from the extraction devices and prefiltered into Surecell ™ disposable test devices having the requisite membranes. The final concentrations of elementary bodies added to the wells were 0 (Control), 100, 250 and 500 pg.

The wells were washed twice (160 μl each), and the anti-chlamydial antibody composition (80 μl) was added to the sample and positive controls only of each device while the anti-creatine kinase-MB antibody composition (80 μl) was added to the negative control well of each device. After two minutes incubation at room temperature, the wells were washed again twice. The peroxidase-labeled anti-antibody composition (80 μl) was then added to all wells followed by 5 minutes incubation at room temperature.

After washing each well twice more, the dye-providing composition (80 μl) was added to all wells, followed by incubation at room temperature for 5 minutes.

The dye resulting from reaction of the leuco dye, hydrogen peroxide and peroxidase on the membranes was visually graded on a scale of 0 to 10 (0 being no dye and 10 being highest density). The results, shown graphically in FIG. 1, indicate that the use of Loprodyne ™ membranes in the test devices resulted in lower backgrounds (see the 0 level of elementary bodies) while maintaining acceptable detection limits and sensitivities.

EXAMPLE 2

Effect of Various Membranes in Assay After Room Temperature Keeping Tests

This example compares the results of assays performed as in Example 1 after the test kits had been stored at room temperature for 10 weeks, which is about twice the normal keeping limits for prior art products.

Figure 2:
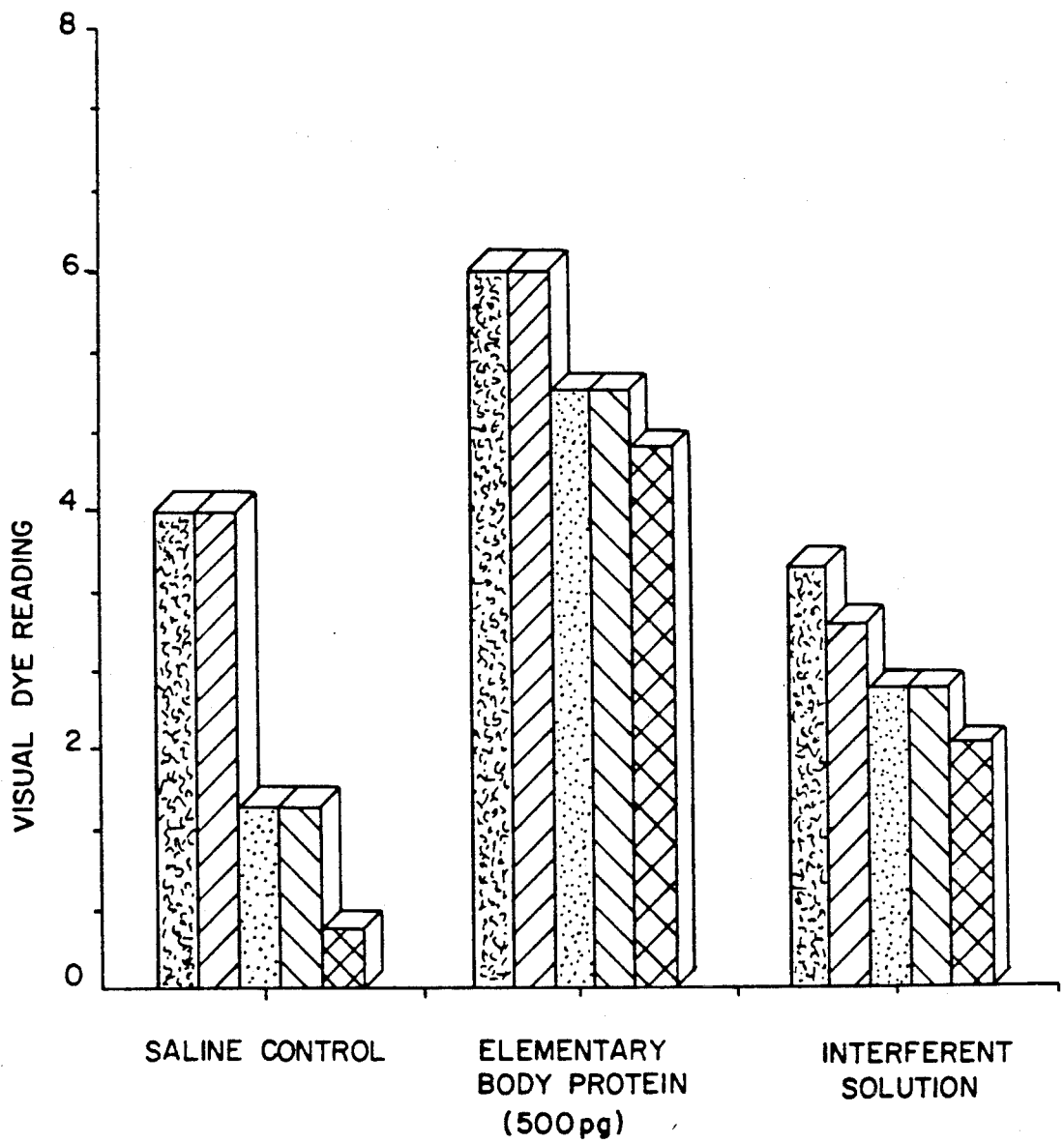
FIG. 2 is a bar graph showing the difference in room temperature keeping for the assays described in Example 3 below.

The assays were carried out with only one concentration of elementary bodies (500 pg), and a sample of the interferent solution was included. The results, graphically illustrated in FIG. 2, show that the background levels (graded 4) are unacceptable for the assays using the Biodyne ™ A membranes, but are acceptable for the assays of this invention. In addition, the assay of this invention showed no loss in sensitivity compared to a control using fresh reagents.

EXAMPLE 3

Comparison of Test Kits After Accelerated Keeping of Reagents

This example compares an assay of the present invention with an assay carried out using a Biodyne ™ A membrane coated with Zonyl ™ FSN nonionic surfactant using labeled anti-antibody which had been kept at various temperatures for 14 days.

The assays were carried out using the protocol described in Example 1 using peroxidase-labeled goat anti-mouse which had been kept for 14 days at 0°, 35° and 42° C. (equivalent to about 60 days at room temperature). Phosphate buffered saline solution was used as a background control, and the elementary bodies concentration for all assays was 500 pg.

Figure 3:
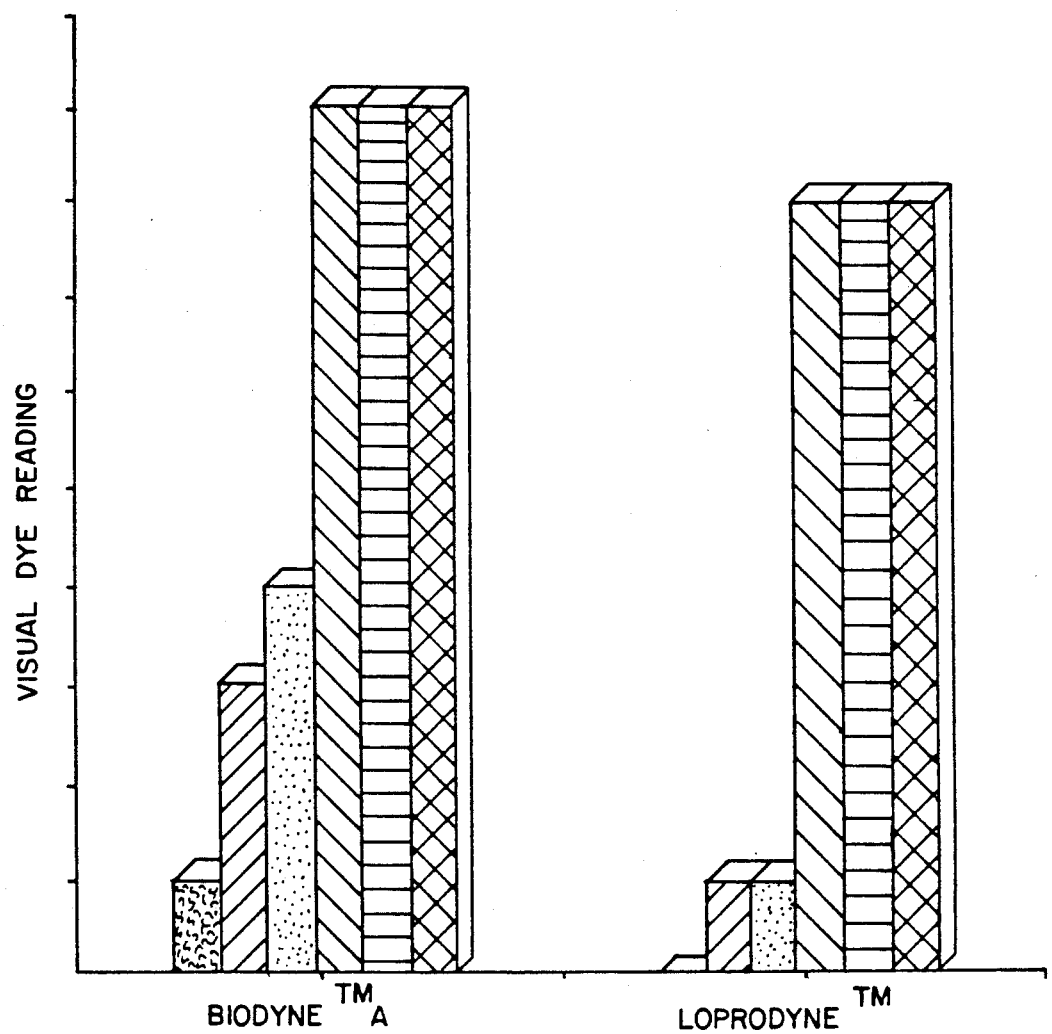
FIG. 3 is a bar graph illustrating the effect of higher temperature keeping tests on background levels for the compared assays of Example 4 below.

The results of the assays are illustrated graphically in FIG. 3. They indicate that as the antibody conjugate was kept at higher temperatures, the background in the assay increased where Biodyne ™ A membranes were used. The assays of this invention showed low backgrounds even at 42° C.

EXAMPLE 4

Comparison with Various Membranes After Accelerated Keeping of Various Reagents This comparison is similar to that of Example 3 except the unlabeled anti-chlamydial antibody and anti-creatine kinase-MB reagents were kept at 42° C. for 7 days. The assays were run using phosphate buffered saline solution for background control, 500 pg elementary bodies and the interferent solution.

The results, provided in FIG. 4, indicate that the backgrounds are unacceptable in assays using both samples of Biodyne ™ A membranes, but highly desirable in assays using Loprodyne ™ membranes.

The invention has been described in detail with particular reference to preferred embodiments thereof, but it will be understood that variations and modifications can be effected within the spirit and scope of the invention.

We claim:

1. A method for the determination of a chlamydial antigen comprising:
   A. contacting chlamydial antigen extracted from a specimen suspected of containing chlamydial organisms with a polyamide microporous filtration membrane having a plurality of hydroxy groups on the surface thereof, and which has an average pore size of from about 1 to about 10 μmeter, for a sufficient time to bind said extracted antigen to said membrane,
   B. contacting chlamydial antigen bound to said membrane with chlamydial antibody so as to form an immunological complex on said membrane, and
   C. determining the presence of said complex on said membrane as a measure of the presence of chlamydial organisms in said specimen.

2. The method of claim 1 wherein said membrane is composed of a polyhexamethylene adipamide which has been treated to add said hydroxy groups to the surface thereof.

3. The method of claim 2 wherein said polyhexamethylene adipamide has been treated with a polymeric material prepared from at least one polymerizable monomer having at least one hydroxy group.

4. The method of claim 1 wherein said membrane has an average pore size of from about 4 to about 8 μmeters.

5. The method of claim 1 for the determination of a chlamydial antigen.

6. The method of claim 5 for the determination of a lipopolysaccharide from a chlamydial organism.

7. The method of claim 1 wherein said chlamydial antibody is enzyme-labeled, and said complex determination is accomplished using a dye-providing composition which comprises a substrate for said enzyme.

8. The method of claim 1 wherein said chlamydial antibody is unlabeled, and said immunological complex is determined using a labeled antibody which is directed to the chlamydial antibody.

9. The method of claim 8 wherein said antichlamydial antibody is labeled with an enzyme, and said complex determination is accomplished using a dye-providing composition which comprises a substrate for said enzyme.

10. The method of claim 9 wherein said enzyme label is peroxidase, and said dye-providing composition comprises a leuco dye which provides a dye in the presence of hydrogen peroxide and peroxidase.

11. A method for the determination of chlamydial organisms comprising:
   A. extracting chlamydial antigen from chlamydial organisms in a biological specimen,
   B. contacting said extracted chlamydial antigen with a polyamide microporous filtration membrane having a plurality of hydroxy groups on the surface thereof, and which has an average pore size of from about 1 to about 10 μmeter,
   C. within about 5 minutes of said contacting step B, contacting said bound chlamydial antigen with an unlabeled chlamydial antibody so as to form an unlabeled immunological complex bound to said membrane,
   D. separating unbound materials in said specimen from said bound complex,
   E. contacting said bound complex with a labeled antibody to said chlamydial antibody so as to form a labeled bound immunological complex,
   F. within about 5 minutes of said contacting step E, separating unbound materials from said bound labeled complex, and
   G. determining the presence of said bound labeled complex as a measure of the presence of chlamydial organisms in said specimen.

12. The method of claim 11 for the determination of *Chlamydia trachomatis*.

13. The method of claim 11 wherein said membrane is composed of a polyhexamethylene adipamide which has been treated to add said hydroxy groups to the surface thereof.

14. The method of claim 13 wherein said polyhexamethylene adipamide has been treated with a polymeric material prepared from at least one polymerizable monomer having at least one hydroxy group.

15. The method of claim 11 wherein said membrane has an average pore size of from about 4 to about 8 μmeters.

16. The method of claim 11 wherein said antichlamydial antibody is labeled with peroxidase, and said bound complex determination is accomplished by contacting it with a composition comprising a leuco dye which provides a dye in the presence of peroxidase and hydrogen peroxide.

17. The method of claim 11 which is carried out within about 25 minutes.

18. A diagnostic test kit useful for the determination of a chlamydial antigen comprising:
   a) a polyamide microporous filtration membrane having a plurality of hydroxy groups on the suface thereof, and which has an average pore size of from about 1 to about 10 μmeter, and
   b) a reagent composition comprising antibodies to a chlamydial antigen.

19. The kit of claim 18 wherein said membrane is provided as part of a disposable test device.

20. The kit of claim 18 wherein said membrane is prepared from polyhexamethylene adipamide which has been treated to add said hydroxy groups to the surface thereof.

* * * * *